(12) United States Patent
Zones et al.

(10) Patent No.: US 9,505,627 B1
(45) Date of Patent: Nov. 29, 2016

(54) PROCESSES USING MOLECULAR SIEVE SSZ-27

(71) Applicant: Chevron U.S.A. Inc., San Ramon, CA (US)

(72) Inventors: Stacey Ian Zones, San Francisco, CA (US); Dan Xie, Richmond, CA (US); Robert James Saxton, Pleasanton, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 15/098,450

(22) Filed: Apr. 14, 2016

Related U.S. Application Data

(60) Provisional application No. 61/165,061, filed on May 21, 2015.

(51) Int. Cl.
| | | |
|---|---|---|
| *C01B 39/46* | (2006.01) | |
| *B01D 53/94* | (2006.01) | |
| *B01D 53/56* | (2006.01) | |
| *B01J 29/70* | (2006.01) | |
| *B01J 29/06* | (2006.01) | |
| *C07C 1/24* | (2006.01) | |
| *C07C 209/16* | (2006.01) | |

(52) U.S. Cl.
CPC ............ *C01B 39/46* (2013.01); *B01D 53/9413* (2013.01); *B01D 53/9486* (2013.01); *B01J 29/061* (2013.01); *B01J 29/70* (2013.01); *C07C 1/24* (2013.01); *C07C 209/16* (2013.01); *B01D 2255/50* (2013.01); *C07C 2529/70* (2013.01); *C07C 2529/72* (2013.01)

(58) Field of Classification Search
CPC ... C01B 39/46; B01D 53/94; B01D 2311/00; B01D 53/56; B01J 29/70; B01J 29/06; C07C 1/24; C07C 209/16
See application file for complete search history.

(56) References Cited

U.S. PATENT DOCUMENTS

| | | | |
|---|---|---|---|
| 8,383,080 B2 * | 2/2013 | Cao ...................... | B01J 29/7015 423/700 |
| 2016/0068400 A1 * | 3/2016 | Davis ...................... | C01B 39/46 423/718 |

\* cited by examiner

*Primary Examiner* — Timothy Vanoy

(57) ABSTRACT

Uses for a new crystalline molecular sieve designated SSZ-27 are disclosed. SSZ-27 is synthesized using a hexamethyl [4.3.3.0] propellane-8,11-diammonium cation as a structure directing agent.

15 Claims, No Drawings

PROCESSES USING MOLECULAR SIEVE SSZ-27

TECHNICAL FIELD

This disclosure relates to uses for a new crystalline molecular sieve designated SSZ-27, a method for preparing SSZ-27, and uses for SSZ-27.

BACKGROUND

Molecular sieves are a class of important materials used in the chemical industry for processes such as gas stream purification and hydrocarbon conversion processes. Molecular sieves are porous solids having interconnected pores of different sizes. Molecular sieves typically have a one-, two- or three-dimensional crystalline pore structure having pores of one or more molecular dimensions that selectively adsorb molecules that can enter the pores, and exclude those molecules that are too large. The pore size, pore shape, interstitial spacing or channels, composition, crystal morphology and structure are a few characteristics of molecular sieves that determine their use in various hydrocarbon adsorption and conversion processes.

For the petroleum and petrochemical industries, the most commercially useful molecular sieves are known as zeolites. A zeolite is an aluminosilicate having an open framework structure formed from corner-sharing the oxygen atoms of $[SiO_4]$ and $[AlO_4]$ tetrahedra. Mobile extra framework cations reside in the pores for balancing charges along the zeolite framework. These charges are a result of substitution of a tetrahedral framework cation (e.g., $Si^{4+}$) with a trivalent or pentavalent cation. Extra framework cations counterbalance these charges preserving the electroneutrality of the framework, and these cations are exchangeable with other cations and/or protons.

Synthetic molecular sieves, particularly zeolites, are typically synthesized by mixing sources of alumina and silica in an aqueous media, often in the presence of a structure directing agent or templating agent. The structure of the molecular sieve formed is determined in part by the solubility of the various sources, the silica-to-alumina ratio, the nature of the cation, the synthesis conditions (temperature, pressure, mixing agitation), the order of addition, the type of structure directing agent, and the like.

Although many different crystalline molecular sieves have been discovered, there is a continuing need for new molecular sieves with desirable properties for gas separation and drying, hydrocarbon and chemical conversions, and other applications. New molecular sieves may contain novel internal pore architectures, providing enhanced selectivities in these processes.

SUMMARY

The present disclosure is directed to uses for a new family of molecular sieves with unique properties, referred to herein as "molecular sieve SSZ-27" or simply "SSZ-27."

In one aspect, there is provided a crystalline molecular sieve having, in its calcined form, the X-ray diffraction lines of Table 3.

In another aspect, there is provided a method of preparing a crystalline molecular sieve by contacting under crystallization conditions (1) at least one source of silicon; (2) at least one source of aluminum; (3) at least one source of an element selected from Groups 1 and 2 of the Periodic Table; (4) hydroxide ions; and (5) hexamethyl [4.3.3.0] propellane-8,11-diammonium cations.

In yet another aspect, there is provided a process for preparing a crystalline molecular sieve having, in its as-synthesized form, the X-ray diffraction lines of Table 2, by: (a) preparing a reaction mixture containing (1) at least one source of silicon; (2) at least one source of aluminum; (3) at least one source of an element selected from Groups 1 and 2 of the Periodic Table; (4) hydroxide ions; (5) hexamethyl [4.3.3.0] propellane-8,11-diammonium cations; and (6) water; and (b) subjecting the reaction mixture to crystallization conditions sufficient to form crystals of the molecular sieve.

The present disclosure also provides a novel molecular sieve designated SSZ-27 having, in its as-synthesized, anhydrous form, a composition, in terms of mole ratios, in the range: $Al_2O_3$: 20-80 $SiO_2$ or more preferably: $Al_2O_3$: 20-35 $SiO_2$.

The present disclosure provides processes using molecular sieve SSZ-27.

DETAILED DESCRIPTION

Introduction

In preparing SSZ-27, a hexamethyl [4.3.3.0] propellane-8,11-diammonium cation is used as a structure directing agent ("SDA"), also known as a crystallization template. The SDA useful for making SSZ-27 has the following structure (1):

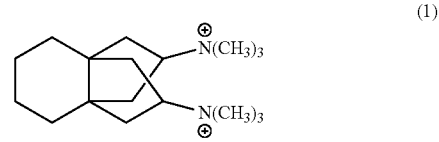

hexamethyl [4.3.3.0] propellane-8, 11-diammonium cation including syn, syn; syn, anti; and anti, anti orientations of the ammonium groups.

The SDA dication is associated with anions which may be any anion that is not detrimental to the formation of SSZ-27. Representative anions include elements from Group 17 of the Periodic Table (e.g., fluoride, chloride, bromide and iodide), hydroxide, sulfate, tetrafluoroboroate, acetate, carboxylate, and the like. As used herein, the numbering scheme for the Periodic Table Groups is as disclosed in *Chem. Eng. News,* 63(5), 27 (1985).

Reaction Mixture

In general, SSZ-27 is prepared by: (a) preparing a reaction mixture containing (1) at least one source of silicon; (2) at least one source of aluminum; (3) at least one source of an element selected from Groups 1 and 2 of the Periodic Table; (4) hydroxide ions; (5) hexamethyl [4.3.3.0] propellane-8, 11-diammonium cations; and (6) water; and (b) subjecting the reaction mixture to crystallization conditions sufficient to form crystals of the molecular sieve.

The composition of the reaction mixture from which the molecular sieve is formed, in terms of mole ratios, is identified in Table 1 below

TABLE 1

| Components | Broad | Exemplary |
| --- | --- | --- |
| $SiO_2/Al_2O_3$ | 20 to 80 | 20 to 35 |
| $M/SiO_2$ | 0.05 to 0.50 | 0.15 to 0.30 |
| $Q/SiO_2$ | 0.10 to 0.40 | 0.10 to 0.30 |
| $OH/SiO_2$ | 0.25 to 0.60 | 0.25 to 0.50 |
| $H_2O/SiO_2$ | 10 to 60 | 20 to 50 | wherein Q is a hexamethyl [4.3.3.0] propellane-8,11-diammonium cation and M is selected from the group consisting of elements from Groups 1 and 2 of the Periodic Table.

Sources useful herein for silicon include fumed silica, precipitated silicates, silica hydrogel, silicic acid, colloidal silica, tetra-alkyl orthosilicates (e.g., tetraethyl orthosilicate), and silica hydroxides.

Sources useful for aluminum include oxides, hydroxides, acetates, oxalates, ammonium salts and sulfates of aluminum. Typical sources of aluminum oxide include aluminates, alumina, and aluminum compounds such as aluminum chloride, aluminum sulfate, aluminum hydroxide, kaolin clays, and other zeolites. An example of the source of aluminum oxide is zeolite Y.

As described herein above, for each embodiment described herein, the reaction mixture can be formed using at least one source of an element selected from Groups 1 and 2 of the Periodic Table (referred to herein as M). In one sub-embodiment, the reaction mixture is formed using a source of an element from Group 1 of the Periodic Table. In another sub-embodiment, the reaction mixture is formed using a source of sodium (Na). Any M-containing compound which is not detrimental to the crystallization process is suitable. Sources for such Groups 1 and 2 elements include oxides, hydroxides, nitrates, sulfates, halides, acetates, oxalates, and citrates thereof.

For each embodiment described herein, the molecular sieve reaction mixture can be supplied by more than one source. Also, two or more reaction components can be provided by one source.

The reaction mixture can be prepared either batch wise or continuously. Crystal size, morphology and crystallization time of the molecular sieve described herein can vary with the nature of the reaction mixture and the crystallization conditions.

Crystallization and Post-Synthesis Treatment

In practice, the molecular sieve is prepared by: (a) preparing a reaction mixture as described herein above; and (b) subjecting the reaction mixture to crystallization conditions sufficient to form crystals of the molecular sieve (see, e.g., H. Robson, *Verified Syntheses of Zeolitic Materials*, Second Revised Edition, Elsevier, 2001).

The reaction mixture is maintained at an elevated temperature until the crystals of the molecular sieve are formed. The hydrothermal crystallization is usually conducted under pressure, and usually in an autoclave so that the reaction mixture is subject to autogenous pressure, at a temperature between 150° C. and 180° C., e.g., from 170° C. to 175° C.

The reaction mixture can be subjected to mild stirring or agitation during the crystallization step. It will be understood by one skilled in the art that the molecular sieves described herein can contain impurities, such as amorphous materials, unit cells having framework topologies which do not coincide with the molecular sieve, and/or other impurities (e.g., organic hydrocarbons).

During the hydrothermal crystallization step, the molecular sieve crystals can be allowed to nucleate spontaneously from the reaction mixture. The use of crystals of the molecular sieve as seed material can be advantageous in decreasing the time necessary for complete crystallization to occur. In addition, seeding can lead to an increased purity of the product obtained by promoting the nucleation and/or formation of the molecular sieve over any undesired phases. When used as seeds, seed crystals are added in an amount between 1% and 10% of the weight of the source for silicon used in the reaction mixture.

Once the molecular sieve crystals have formed, the solid product is separated from the reaction mixture by standard mechanical separation techniques such as filtration. The crystals are water-washed and then dried to obtain the as-synthesized molecular sieve crystals. The drying step can be performed at atmospheric pressure or under vacuum.

The molecular sieve can be used as-synthesized, but typically will be thermally treated (calcined). The term "as-synthesized" refers to the molecular sieve in its form after crystallization, prior to removal of the SDA cation. The SDA can be removed by thermal treatment (e.g., calcination), preferably in an oxidative atmosphere (e.g., air, gas with an oxygen partial pressure of greater than 0 kPa) at a temperature readily determinable by one skilled in the art sufficient to remove the SDA from the molecular sieve. The SDA can also be removed by photolysis techniques (e.g., exposing the SDA-containing molecular sieve product to light or electromagnetic radiation that has a wavelength shorter than visible light under conditions sufficient to selectively remove the organic compound from the molecular sieve) as described in U.S. Pat. No. 6,960,327.

The molecular sieve can subsequently be calcined in steam, air or inert gas at temperatures ranging from 200° C. to 800° C. for periods of time ranging from 1 to 48 hours, or more. Usually, it is desirable to remove the extra-framework cation (e.g., $Na^+$) by ion exchange and replace it with hydrogen, ammonium, or any desired metal-ion. Particularly preferred cations are those which tailor the catalytic activity for certain hydrocarbon conversion reactions. These include hydrogen, rare earth metals and metals of Groups 2 to 15 of the Periodic Table of the Elements.

Where the molecular sieve formed is an intermediate material, the target molecular sieve can be achieved using post-synthesis techniques such as heteroatom lattice substitution techniques in order to achieve a higher $SiO_2/Al_2O_3$ ratio. The target molecular sieve can also be achieved by removing heteroatoms from the lattice by known techniques such as acid leaching.

The molecular sieve made from the process disclosed herein can be formed into a wide variety of physical shapes. Generally speaking, the molecular sieve can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, the molecular sieve can be extruded before drying or dried (or partially dried) and then extruded.

The molecular sieve can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. Nos. 4,910,006 and 5,316,753.

Characterization of the Molecular Sieve

SSZ-27 has, in its as-synthesized, anhydrous form, a composition, in terms of mole ratios, in the range: $Al_2O_3$: 20-80 $SiO_2$ or more preferably: $Al_2O_3$: 20-35 $SiO_2$.

Molecular sieves synthesized by the process disclosed herein are characterized by their X-ray diffraction (XRD) pattern. The product of the synthesis reaction is a crystalline molecular sieve containing within its pore structure hexamethyl [4.3.3.0] propellane-8,11-diammonium cations. The resultant as-synthesized material has an X-ray diffraction pattern which is distinguished from the patterns of other known as-synthesized or thermally treated crystalline materials by the lines listed in Table 2 below.

TABLE 2

Characteristic Peaks for As-Synthesized SSZ-27

| 2-Theta[a] | d-Spacing, nm | Relative Intensity[b] |
|---|---|---|
| 7.57 | 1.167 | W |
| 8.62 | 1.025 | W |
| 9.35 | 0.946 | M |
| 9.83 | 0.900 | W |
| 13.55 | 0.653 | W |
| 14.80 | 0.598 | W |
| 15.27 | 0.580 | W |
| 16.25 | 0.545 | W |
| 17.72 | 0.500 | W |
| 19.76 | 0.449 | M |
| 20.50 | 0.433 | W |
| 21.08 | 0.421 | S |
| 21.30 | 0.417 | M |
| 21.93 | 0.405 | S |
| 22.95 | 0.387 | VS |

[a]±0.20
[b]The powder XRD patterns provided are based on a relative intensity scale in which the strongest line in the powder X-ray pattern is assigned a value of 100: W = weak (>0 to ≤20); M = medium (>20 to ≤40); S = strong (>40 to ≤60); VS = very strong (>60 to ≤100).

The X-ray diffraction pattern of the calcined form of SSZ-27 includes the lines listed in Table 3 below:

TABLE 3

Characteristic Peaks for Calcined SSZ-27

| 2-Theta[a] | d-Spacing, nm | Relative Intensity[b] |
|---|---|---|
| 7.50 | 1.177 | W |
| 8.65 | 1.021 | W |
| 9.47 | 0.933 | VS |
| 9.94 | 0.889 | M |
| 13.47 | 0.657 | M |
| 14.86 | 0.596 | M |
| 16.07 | 0.551 | W |
| 16.37 | 0.541 | W |
| 17.92 | 0.495 | W |
| 19.92 | 0.445 | W |
| 20.66 | 0.430 | W |
| 21.14 | 0.420 | W |
| 21.34 | 0.416 | W |
| 22.07 | 0.402 | M |
| 23.17 | 0.384 | M |

[a]±0.20
[b]The powder XRD patterns provided are based on a relative intensity scale in which the strongest line in the powder X-ray pattern is assigned a value of 100: W = weak (>0 to ≤20); M = medium (>20 to ≤40); S = strong (>40 to ≤60); VS = very strong (>60 to ≤100).

The powder X-ray diffraction patterns presented herein were collected by standard techniques. The radiation was CuIl, radiation. The peak heights and the positions, as a function of 2θ where θ is the Bragg angle, were read from the relative intensities of the peaks (adjusting for background), and d, the interplanar spacing corresponding to the recorded lines, can be calculated.

Minor variations in the diffraction pattern can result from variations in the mole ratios of the framework species of the particular sample due to changes in lattice constants. In addition, sufficiently small crystals will affect the shape and intensity of peaks, leading to significant peak broadening. Minor variations in the diffraction pattern can also result from variations in the organic compound used in the preparation. Calcination can also cause minor shifts in the XRD pattern. Notwithstanding these minor perturbations, the basic crystal lattice structure remains unchanged.

Processes Using SSZ-27

SSZ-27 is useful as an adsorbent for gas separations. SSZ-27 can also be used as a catalyst for converting oxygenates (e.g., methanol) to olefins and for making small amines. SSZ-27 can be used to reduce oxides of nitrogen in a gas streams, such as automobile exhaust. SSZ-27 can also be used to as a cold start hydrocarbon trap in combustion engine pollution control systems. SSZ-27 is particularly useful for trapping $C_3$ fragments.

Gas Separation

SSZ-100 can be used to separate gases. For example, it can be used to separate carbon dioxide from natural gas. Typically, the molecular sieve is used as a component in a membrane that is used to separate the gases. Examples of such membranes are disclosed in U.S. Pat. No. 6,508,860.

Oxygenate Conversion

SSZ-27 is useful in the catalytic conversion of oxygenates to one or more light olefins, i.e., $C_2$, $C_3$ and/or $C_4$ olefins. As used herein, the term "oxygenates" is defined to include aliphatic alcohols, ethers, carbonyl compounds (aldehydes, ketones, carboxylic acids, carbonates, and the like), and also compounds containing hetero-atoms, such as, halides, mercaptans, sulfides, amines, and mixtures thereof. The aliphatic moiety will normally contain from 1 to 10 carbon atoms, such as from 1 to 4 carbon atoms.

Representative oxygenates include lower straight chain or branched aliphatic alcohols, their unsaturated counterparts, and their nitrogen, halogen and sulfur analogues. Examples of suitable oxygenate compounds include methanol, ethanol, n-propanol, isopropanol, $C_4$-$C_{10}$ alcohols, methyl ethyl ether, dimethyl ether, diethyl ether, diisopropyl ether, methyl mercaptan, methyl sulfide, methyl amine, ethyl mercaptan, diethyl sulfide, diethyl amine, ethyl chloride, formaldehyde, dimethyl carbonate, dimethyl ketone, acetic acid, n-alkyl amines, n-alkyl halides, n-alkyl sulfides having n-alkyl groups of comprising the range of from 3 to 10 carbon atoms, and mixtures thereof. Particularly suitable oxygenate compounds are methanol, dimethyl ether, or mixtures thereof, most preferably methanol. As used herein, the term "oxygenate" designates only the organic material used as the feed. The total charge of feed to the reaction zone may contain additional compounds, such as diluents.

In the present oxygenate conversion process, a feedstock comprising an organic oxygenate, optionally with one or more diluents, is contacted in the vapor phase in a reaction zone with a catalyst comprising the molecular sieve disclosed herein at effective process conditions so as to produce the desired olefins. Alternatively, the process may be carried out in a liquid or a mixed vapor/liquid phase. When the process is carried out in the liquid phase or a mixed vapor/liquid phase, different conversion rates and selectivities of feedstock-to-product may result depending upon the catalyst and the reaction conditions.

When present, the diluent(s) is generally non-reactive to the feedstock or molecular sieve catalyst composition and is typically used to reduce the concentration of the oxygenate in the feedstock. Non-limiting examples of suitable diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. Diluent(s) may comprise from 1 to 99 mole % of the total feed mixture.

The temperature employed in the oxygenate conversion process may vary over a wide range, such as from 200° C. to 1000° C. (e.g., from 250° C. to 800° C., from 250° C. to 750° C., from 300° C. to 650° C., from 350° C. to 600° C., or from 400° C. to 600° C.).

Light olefin products will form, although not necessarily in optimum amounts, at a wide range of pressures, including autogenous pressures and pressures in the range of from 0.1 to 10 MPa (e.g., from 7 kPa to 5 MPa, or from 50 kPa to 1 MPa). The foregoing pressures are exclusive of diluent, if any is present, and refer to the partial pressure of the feedstock as it relates to oxygenate compounds and/or mixtures thereof. Lower and upper extremes of pressure may adversely affect selectivity, conversion, coking rate, and/or reaction rate; however, light olefins such as ethylene still may form.

The process should be continued for a period of time sufficient to produce the desired olefin products. The reaction time may vary from tenths of seconds to a number of hours. The reaction time is largely determined by the reaction temperature, the pressure, the catalyst selected, the weight hourly space velocity, the phase (liquid or vapor) and the selected process design characteristics.

A wide range of weight hourly space velocities (WHSV) for the feedstock will function in the present process. WHSV is defined as weight of feed (excluding diluent) per hour per weight of a total reaction volume of molecular sieve catalyst (excluding inerts and/or fillers). The WHSV generally should be in the range of from 0.01 $h^{-1}$ to 500 $h^{-1}$ (e.g., from about 0.5 to 300 $h^{-1}$, or from 0.1 to 200 $h^{-1}$).

The molecular sieve catalyst can be incorporated into solid particles in which the catalyst is present in an amount effective to promote the desired conversion of oxygenates to light olefins. In one aspect, the solid particles comprise a catalytically effective amount of the catalyst and at least one matrix material selected from the group consisting of binder materials, filler materials and mixtures thereof to provide a desired property or properties, e.g., desired catalyst dilution, mechanical strength and the like to the solid particles. Such matrix materials are often, to some extent, porous in nature and can or cannot be effective to promote the desired reaction. Filler and binder materials include, for example, synthetic and naturally occurring substances such as metal oxides, clays, silicas, aluminas, silica-aluminas, silica-magnesias, silica-zirconias, silica-thorias and the like. If matrix materials are included in the catalyst composition, the molecular sieve desirably comprises from 1 to 99 wt. % (e.g., from 5 to 90 wt. % or from 10 to 80 wt. %) of the total composition.

Synthesis of Amines

SSZ-27 can be used in a catalyst to prepare methylamine or dimethylamine. Dimethylamine is generally prepared in industrial quantities by continuous reaction of methanol (and/or dimethyl ether) and ammonia in the presence of a silica-alumina catalyst. The reactants are typically combined in the vapor phase, at temperatures of from 300° C. to 500° C., and at elevated pressures. Such a process is disclosed in U.S. Pat. No. 4,737,592.

The catalyst is used in its acid form. Acid forms of molecular sieves can be prepared by a variety of techniques. Desirably, the molecular sieve used to prepare dimethylamine will be in the hydrogen form, or have an alkali or alkaline earth metal, such as Na, K, Rb, or Cs, ion-exchanged into it.

The process disclosed herein involves reacting methanol, dimethyl ether, or a mixture thereof and ammonia in amounts sufficient to provide a carbon/nitrogen (C/N) ratio of from 0.2 to 1.5, e.g., from 0.5 to 1.2. The reaction is conducted at a temperature of from 250° C. to 450° C., e.g., from 300° C. to 400° C. Reaction pressures can vary from 7 to 7000 kPa, e.g., from 70 to 3000 kPa. A methanol and/or dimethyl ether space time of from 0.01 to 80 $h^{-1}$ (e.g., from 0.10 to 1.5 $h^{-1}$) is typically used. This space time is calculated as the mass of catalyst divided by the mass flow rate of methanol/dimethyl ether introduced into the reactor.

Reduction of Oxides of Nitrogen

SSZ-27 can be used for the catalytic reduction of the oxides of nitrogen in a gas stream. The catalyst comprises one or more metals supported on the molecular sieve support. Any suitable metal may be selected. Metals particularly effective for use during selective catalytic reduction include metals selected from the group consisting of Cr, Mn, Re, Mo, Fe, Ru, Co, Rh, Ir, Ni, Pd, Pt, Cu, Ag, Zn, Ga, In, Sn, and mixtures thereof. In one embodiment, the one or more metals is selected from the group consisting of Cr, Mn, Fe, Co, Rh, Ni, Pd, Pt, Cu, and mixtures thereof. Preferably, the metal is selected from Mn, Fe, Co, Pt, and Cu. More preferably, the one or more metals may be selected from the group consisting of Fe, Cu, and mixtures thereof. In an exemplary embodiment, the metal is Cu.

Any suitable and effective amount of at least one metal may be used in the catalyst. The total amount of the metal(s) that may be included in the molecular sieve may be from 0.01 to 20 wt. % (e.g., from 0.1 to 10 wt. %, from 0.5 to 5 wt. %, from 1 to 3 wt. %, or from 1.5 to 2.5 wt. %), based on the total weight of the catalyst.

The molecular sieve acts as a support for the metal, e.g., the metal may be inside the pore(s) and/or may be on the external surface of the molecular sieve. In an exemplary embodiment, a significant amount of the metal(s) resides inside the pores.

The metal(s) may also be included in the molecular sieve and/or supported by the molecular sieve using any feasible method. For example, the metal can be added after the molecular sieve has been synthesized, e.g., by incipient wetness or exchange process; or can be added during molecular sieve synthesis.

The molecular sieve catalysts may be used in any suitable form. For example, the molecular sieve catalyst may be used in powder form, as extrudates, as pellets, or in any other suitable form.

The molecular sieve catalysts for use herein may be coated on a suitable substrate monolith or can be formed as extruded-type catalysts, but are preferably used in a catalyst coating. In one embodiment, the molecular sieve catalyst is coated on a flow-through monolith substrate (i.e., a honeycomb monolithic catalyst support structure with many small, parallel channels running axially through the entire part) or filter monolith substrate, such as a wall-flow filter, etc. The molecular sieve catalyst for use herein may be coated, e.g., as a washcoat component, on a suitable monolith substrate, such as a metal or ceramic flow through monolith substrate or a filtering substrate, such as a wall-flow filter or sintered metal or partial filter (such as those disclosed in WO 01/80978 or EP 1057519). Alternatively, the molecular sieves for use herein may be synthesized directly onto the substrate and/or may be formed into an extruded-type flow through catalyst.

Washcoat compositions containing the molecular sieves for use herein for coating onto the monolith substrate for manufacturing extruded type substrate monoliths may comprise a binder, such as alumina, silica, (non-molecular sieve) silica-alumina, naturally occurring clays, such as $TiO_2$, $ZrO_2$, $SnO_2$, $CeO_2$, or mixtures thereof.

According to one embodiment, a method of using the catalyst comprises exposing a catalyst to at least one reactant in a chemical process. In other words, a method for reducing $NO_x$ in a gas comprises exposing the gas having at least one reactant, such as $NO_x$, to a catalyst. As used herein, a chemical process for reducing $NO_x$ in a gas can include any suitable chemical process using a catalyst comprising a molecular sieve or zeolite. Typical chemical processes include, but are not limited to, exhaust gas treatment such as selective catalytic reduction using nitrogenous reductants, lean $NO_x$ catalyst, catalyzed soot filter, or a combination of any one of these with a $NO_x$ adsorber catalyst or a three-way catalyst (TWC), e.g., NAC+(downstream)SCR or TWC+(downstream)SCR.

A method of treating $NO_x$ in an exhaust gas of a lean burn internal combustion engine is to store the $NO_x$ from a lean gas in a basic material and then to release the $NO_x$ from the basic material and reduce it periodically using a rich gas. The combination of a basic material (such as an alkali metal, alkaline earth metal, or a rare earth metal), and a precious metal (such as platinum), and possibly also a reduction catalyst component (such as rhodium) is typically referred to as a $NO_x$ adsorber catalyst (NAC), a lean $NO_x$ trap (LNT), or a $NO_x$ storage/reduction catalyst (NSRC). As used herein, $NO_x$ storage/reduction catalyst, $NO_x$ trap, and $NO_x$ adsorber catalyst (or their acronyms) may be used interchangeably.

Under certain conditions, during the periodically rich regeneration events, $NH_3$ may be generated over a $NO_x$ adsorber catalyst. The addition of a SCR catalyst downstream of the $NO_x$ adsorber catalyst may improve the overall system $NO_x$ reduction efficiency. In the combined system, the SCR catalyst is capable of storing the released $NH_3$ from the NAC catalyst during rich regeneration events and utilizes the stored $NH_3$ to selectively reduce some or all of the $NO_x$ that slips through the NAC catalyst during the normal lean operation conditions. As used herein, such combined systems may be shown as a combination of their respective acronyms, e.g., NAC+SCR or LNT+SCR.

The catalysts may be effective in reducing or lean conditions, e.g., as encountered in engine emissions. For example, the lean portion of the cycle may consist of exposure to about 200 ppm $NO_x$, 10% $O_2$, 5% $H_2O$, 5% $CO_2$ in $N_2$, and the rich portion of the cycle may consist of exposure to about 200 ppm $NO_x$, 5000 ppm $C_3H_6$, 1.3% $H_2$, 4% CO, 1% $O_2$, 5% $H_2O$, 5% $CO_2$ in $N_2$. A reducing atmosphere is an atmosphere having a lambda value of less than 1, i.e., the redox composition is net reducing. A lean atmosphere is one having a lambda value of greater than 1, i.e., the redox composition is net oxidizing. The catalysts described herein may be particularly effective when exposed to a reducing atmosphere, more particularly a high temperature reducing atmosphere, such as when encountered during the rich phase of a lean/rich excursion cycle.

A method for reducing $NO_x$ in a gas comprises exposing the gas having at least one reactant to a catalyst. The reactant may include any reactants typically encountered in the chemical processes above. Reactants may include a selective catalytic reductant, such as ammonia. Selective catalytic reduction may include (1) using ammonia or a nitrogenous reductant or (2) a hydrocarbon reductant (the latter also known as lean $NO_x$ catalysis). Other reactants may include nitrogen oxides and oxygen. In an exemplary embodiment, the catalysts described herein are used during selective catalytic reduction of $NO_x$ with ammonia.

The at least one reactant, e.g., nitrogen oxides, is reduced with the reducing agent at a temperature of at least 100° C. (e.g., from 150° C. to 750° C., or from 175° C. to 550° C.).

For a reactant including nitrogen oxides, the reduction of nitrogen oxides may be carried out in the presence of oxygen or in the absence of oxygen. The source of nitrogenous reductant can be ammonia, hydrazine, ammonium carbonate, ammonium carbamate, ammonium hydrogen carbonate, ammonium formate or any suitable ammonia precursor, such as urea.

The method may be performed on a gas derived from a combustion process, such as from an internal combustion engine (whether mobile or stationary), a gas turbine and coal or oil fired power plants. The method may also be used to treat gas from industrial processes such as refining, from refinery heaters and boilers, furnaces, the chemical processing industry, coke ovens, municipal waste plants and incinerators, coffee roasting plants, etc.

In a particular embodiment, the method is used for treating exhaust gas from a vehicular internal combustion engine with a lean/rich cycle, such as a diesel engine, a gasoline engine, or an engine powered by liquid petroleum gas or natural gas.

For a reactant including nitrogen oxides, the nitrogenous reductant may be metered into the flowing exhaust gas only when it is determined that the molecular sieve catalyst is capable of catalyzing $NO_x$ reduction at or above a desired efficiency, such as at above 100° C., above 150° C., or above 175° C. The determination by the control means can be assisted by one or more suitable sensor inputs indicative of a condition of the engine selected from the group consisting of: exhaust gas temperature, catalyst bed temperature, accelerator position, mass flow of exhaust gas in the system, manifold vacuum, ignition timing, engine speed, lambda value of the exhaust gas, the quantity of fuel injected in the engine, the position of the exhaust gas recirculation (EGR) valve and thereby the amount of EGR and boost pressure.

Metering may be controlled in response to the quantity of nitrogen oxides in the exhaust gas determined either directly (using a suitable $NO_x$ sensor) or indirectly, such as using pre-correlated look-up tables or maps—stored in the control means—correlating any one or more of the abovementioned inputs indicative of a condition of the engine with predicted $NO_x$ content of the exhaust gas.

The molecular sieve supported metal catalysts described herein may exhibit improved $NH_3$-SCR activity, good thermal stability, good hydrothermal stability, and tolerate repeated lean/rich high temperature aging.

Treatment of Engine Exhaust (Cold Start Emissions)

SSZ-27 can also be used as a hydrocarbon trap, particularly for reducing the emissions associated with the combustion of hydrocarbon fuels.

Increasingly lower emissions standards for vehicles are forcing automobile and catalyst manufacturers to focus on reducing cold start hydrocarbon emissions since a large portion of hydrocarbon emissions occur during the cold start period. Consequently, control of emissions during the cold start operation of a vehicle containing an internal combustion engine is essential. Vehicles equipped with a conventional three-way catalytic converter typically contain precious metals supported on a washcoat layer, which in turn is deposited on a monolithic carrier. Fresh catalysts start to operate at about 170° C., while aged catalysts work only at about 200° C. to 225° C. These catalysts usually require at least 1-2 minutes before reaching such temperatures, and during this "cold start" period, 70% to 80% of the tailpipe hydrocarbon emissions occur. Such cold start emissions often result in failure in the cycle of the U.S. Federal Test Procedure (FTP), a standardized laboratory method for new vehicles testing that is based on two simulated environments; namely, city and highway, in which prototypes of new vehicle models are driven by a trained driver in a laboratory on a dynamometer. At lower temperatures where the catalyst in a catalytic converter is not able to effectively convert incompletely burned hydrocarbons to final combustion products, a hydrocarbon adsorber system should trap hydrocarbons exhausted from the engine before they reach the catalytic converter by adsorbing the incompletely burned hydrocarbons. In the ideal case, desorption should occur at temperatures exceeding catalyst light-off.

The critical factors for any emission hydrocarbon trap are the adsorption capacity of the adsorbent, the desorption temperature at which adsorbed hydrocarbons are desorbed and passed to the catalytic converter (must be higher than the catalyst operating temperature), and the hydrothermal stability of the adsorbent. Molecular sieves such as zeolites have generally been found to be useful adsorbents for this application in part due to their hydrothermal stability under these conditions compared to other materials.

A method of treating exhaust gas is disclosed that comprises a hydrocarbon combustion product is provided, the method comprising contacting the exhaust gas with molecular sieve SSZ-27 for a time period effective to facilitate adsorption of the hydrocarbon combustion product by the molecular sieve; passing a purge gas through the molecular sieve to remove adsorbed hydrocarbon combustion product therefrom; and contacting the purge gas containing the removed hydrocarbon combustion product with a hydrocarbon conversion catalyst. The phrase "method of treating exhaust gas" generally refers to a method of reducing the emission of exhaust gas pollutants, particularly those associated with the incomplete combustion of hydrocarbon fuels. While not exclusively limited thereto, the treatment method is primarily directed to reducing the emission of incompletely combusted exhaust gas components, such as occur during the cold start operation of an internal combustion engine.

Exhaust gases produced from the combustion of a hydrocarbon fuels in an internal combustion engine contain a plurality of combustion components, typically including linear and branched chain non-aromatic hydrocarbons, cycloaliphatic hydrocarbons, aromatic hydrocarbons, polycyclic hydrocarbons and mixtures thereof, as well as non-hydrocarbon components such as carbon dioxide, water, nitrogen oxides and sulfur dioxide. Included within such emissions compounds are aromatic hydrocarbons such as toluene, xylene, benzene and mixtures thereof; linear and branched hydrocarbons such as methane, ethane, ethylene, propane, propylene, butane, pentane, hexane, heptane, octane; cycloaliphatic hydrocarbons such as cyclohexane; and additional fuel additives such as alcohols and methyl tertiary butyl ether (MTBE). The method disclosed herein may be advantageously utilized to reduce such hydrocarbon emissions, particularly during cold start operation of an internal combustion engine, without being necessarily limited to a particular hydrocarbon fuel. Typical hydrocarbon fuels benefiting from the present invention include gasolines, diesel fuels, aviation fuels, and the like.

The method may be applied as a batch process in which the adsorbent is contacted with the exhaust gas batchwise or as a continuous or semi-continuous process in which the exhaust gas continuously or semi-continuously flows through the molecular sieve. For example, the method may be applied as a continuous process for purifying the exhaust gas from an internal combustion engine in which a hydrocarbon fuel is combusted. In such a continuous process, the exhaust gas may be first passed from the source, such as from an internal combustion engine, to an adsorbent molecular sieve (i.e., SSZ-27), so that components in the exhaust gas, particularly hydrocarbons, are adsorbed by the molecular sieve. Depending on the application, the adsorbed components are typically subsequently desorbed from the molecular sieve and brought into contact with a catalyst. In the case of an exhaust gas purification system, SSZ-27 may be utilized to adsorb partially combusted hydrocarbon components from the exhaust gas of an internal combustion engine by contacting the molecular sieve with the exhaust gas upstream of a catalytic converter. As the molecular sieve and the catalyst subsequently heat up due to continued throughflow of the exhaust gas, the components adsorbed onto the molecular sieve are desorbed into the exhaust gas stream and passed on to the converter. The desorbed hydrocarbon components are then converted by the catalyst due to the improved hydrocarbon conversion efficiency of the catalyst at higher operating temperatures.

The method disclosed herein may also be carried out sequentially and continuously with a flowing exhaust gas, that is, wherein the exhaust gas continuously flows through the molecular sieve and then through a downstream catalytic converter. In this regard, the exhaust gas may also essentially function as the purge gas for removing exhaust components desorbed from the molecular sieve. A separate purge gas stream, or a separate purge gas stream in conjunction with the exhaust gas stream, may also be used to remove the desorbed exhaust gas components, including, without limitation, air such as secondary air that is added to the exhaust gas stream, an inert gas, or a mixture thereof.

The use of SSZ-27 in batch and semi-continuous systems is also within the scope of this disclosure. For example, in a batch process SSZ-27 may be contacted with a portion of the exhaust gas such that the exhaust gas components, particularly incompletely combusted hydrocarbon components produced during cold start operation of an internal combustion engine, are adsorbed onto the molecular sieve. Thereafter, when the operating temperature of a catalyst such as in a catalytic converter has been reached, the adsorbed components may be purged using a purge gas and passed to the catalyst for conversion to exhaust gas emission products. Similarly, in a semi-continuous process, the exhaust gas may be initially passed through the molecular sieve and subsequently through a downstream catalyst. After a period of time (e.g., when the catalyst light-off temperature is reached), the exhaust gas may be re-directed to pass only through the catalyst, such that the molecular sieve is bypassed. A purge gas such as air may then be passed through the molecular sieve to desorb the exhaust gas components adsorbed onto the molecular sieve.

In one embodiment, the SSZ-27 molecular sieve may also contain a metal cation selected from rare earth, Group 2 metals, Groups 6-12 metals, and mixtures thereof (e.g., the metal cation may be selected from Mg, Ca, Mn, Fe, Co, Ni, Pd, Pt, Cu, Ag, Au, Zn, Cd, and mixtures thereof). In an alternate embodiment, the molecular sieve contains a metal selected from Cu, Ag, Au and mixtures thereof.

Although the molecular sieve may be utilized to adsorb exhaust gas components by itself, it may also be utilized in an adsorbent material that comprises the molecular sieve along with additional materials such as binders and clays.

The adsorbent material may also comprise one or more catalysts in conjunction with the molecular sieve. Such catalysts are generally known in the art and are not specifically limited for use herein in conjunction with the adsorbent material. Other adsorbent materials may also be included along with molecular sieve SSZ-27 if desired, including without limitation molecular sieves having a framework type such as, e.g., AEI, AFX, *BEA, CHA, CON, IFR, MTT, MWW, MTW, SEW, SFE, SFF, SFG, SFH, SFN, SFS, *SFV, SSY, STF, STT, -SVR, and mixtures thereof, and the like.

EXAMPLES

The following illustrative examples are intended to be non-limiting.

Example 1

Synthesis of SSZ-27

1 mmole of the SDA in the OH form, in 2.5 g of water, was added into a Teflon liner for a 23 mL Parr reactor. Next, 2 g of 1 N NaOH solution was added, followed by 1 g of water, and Na—Y zeolite (CBV100, Zeolyst International, $SiO_2/Al_2O_3$ mole ratio=5.1) as the aluminum source. Finally, 0.60 g of CAB-O-SIL® M5 fumed silica (Cabot Corporation) was added. The liner was capped and placed within a Parr steel autoclave reactor. The autoclave was then fixed in a rotating spit (43 rpm) within an oven heated at 170° C. for 7-10 days. The solid products were recovered, washed thoroughly with deionized water and dried.

The resulting product was analyzed by powder XRD and indicated that the material is unique.

Example 2

Seeded Synthesis of SSZ-27

Example 1 was repeated with the exception that as-synthesized zeolite from Example 1 was added to the reaction mixture as seed material (2% of the weight of the silicon source). The crystallization was complete in 6-7 days, as confirmed by powder XRD.

Example 3

Calcination of SSZ-27

The as-synthesized product of Example 1 was calcined inside a muffle furnace under a flow of air heated to 595° C. at a rate of 1° C./minute and held at 595° C. for 5 hours, cooled and then analyzed by powder XRD. The powder XRD pattern of the resulting product indicated that the material remains stable after calcination to remove the organic SDA.

Example 4

Ammonium-Ion Exchange of SSZ-27

The calcined material from Example 3 (Na-SSZ-27) was treated with 10 mL (per g of zeolite) of a 1 N ammonium nitrate solution at 90° C. for 2 hours. The solution was cooled, decanted off and the same process repeated.

The product ($NH_4$-SSZ-27) after drying was subjected to a micropore volume analysis using $N_2$ as adsorbate and via the BET method. The zeolite exhibited a micropore volume of 0.11 $cm^3$/g and indicates that SSZ-27 has microporous character.

Example 5

Methanol Conversion

The product made in Example 4 was pelletized at 5 kpsi, crushed and meshed to 20-40. 0.25 g of catalyst (diluted 4:1 v/v with alundum) was centered in a stainless steel downflow reactor in a split tube furnace. The catalyst was preheated in-situ under flowing nitrogen at 400° C. A feed of 10% methanol in nitrogen was introduced into the reactor at a rate of 1.0 $h^{-1}$ WHSV.

Reaction data was collected using a plug flow and an Agilent on-line gas chromatograph with an FID detector. Reaction products were analyzed at 60 minutes and 120 minutes on an HP-PLOT Q column. The results are summarized in Table 4.

TABLE 4

| Product | 1 Hour Data | 2 Hour Data |
| --- | --- | --- |
| Methane | 9.0 | 4.5 |
| Ethane | 13.3 | 2.2 |
| Ethylene | 13.5 | 33.8 |
| Propane | 3.3 | 11.9 |
| Propylene | 4.8 | 28.3 |
| Summed Butanes/Butenes | 11.5 | 13.5 |
| Summed Pentanes/Pentenes | 25.0 | 5.5 |

The products shown in Table 4 are consistent with those for a small pore zeolite in terms of product shape-selectivity in the reaction of methanol being catalytically converted to olefins of mostly $O_2$-$O_4$ size.

As used herein, the term "comprising" means including elements or steps that are identified following that term, but any such elements or steps are not exhaustive, and an embodiment can include other elements or steps.

Unless otherwise specified, the recitation of a genus of elements, materials or other components, from which an individual component or mixture of components can be selected, is intended to include all possible sub-generic combinations of the listed components and mixtures thereof.

All documents cited in this application are herein incorporated by reference in their entirety to the extent such disclosure is not inconsistent with this text.

The invention claimed is:

1. In a process for separating gases using a membrane containing a molecular sieve, the improvement comprising using as the molecular sieve a molecular sieve having in its calcined form, an X-ray diffraction pattern including the lines listed in the following table:

| 2-Theta | d-Spacing, nm | Relative Intensity |
| --- | --- | --- |
| 7.50 ± 0.20 | 1.177 | W |
| 8.65 ± 0.20 | 1.021 | W |
| 9.47 ± 0.20 | 0.933 | VS |
| 9.94 ± 0.20 | 0.889 | M |
| 13.47 ± 0.20 | 0.657 | M |
| 14.86 ± 0.20 | 0.596 | M |
| 16.07 ± 0.20 | 0.551 | W |
| 16.37 ± 0.20 | 0.541 | W |
| 17.92 ± 0.20 | 0.495 | W |
| 19.92 ± 0.20 | 0.445 | W |
| 20.66 ± 0.20 | 0.430 | W |

-continued

| 2-Theta | d-Spacing, nm | Relative Intensity |
| --- | --- | --- |
| 21.14 ± 0.20 | 0.420 | W |
| 21.34 ± 0.20 | 0.416 | W |
| 22.07 ± 0.20 | 0.402 | M |
| 23.17 ± 0.20 | 0.384 | M. |

2. A process for the production of light olefins from a feedstock comprising an oxygenate or mixture of oxygenates, the process comprising reacting the feedstock at effective conditions over a catalyst comprising a molecular sieve having, in its calcined form, an X-ray diffraction pattern including the lines listed in the following table:

| 2-Theta | d-Spacing, nm | Relative Intensity |
| --- | --- | --- |
| 7.50 ± 0.20 | 1.177 | W |
| 8.65 ± 0.20 | 1.021 | W |
| 9.47 ± 0.20 | 0.933 | VS |
| 9.94 ± 0.20 | 0.889 | M |
| 13.47 ± 0.20 | 0.657 | M |
| 14.86 ± 0.20 | 0.596 | M |
| 16.07 ± 0.20 | 0.551 | W |
| 16.37 ± 0.20 | 0.541 | W |
| 17.92 ± 0.20 | 0.495 | W |
| 19.92 ± 0.20 | 0.445 | W |
| 20.66 ± 0.20 | 0.430 | W |
| 21.14 ± 0.20 | 0.420 | W |
| 21.34 ± 0.20 | 0.416 | W |
| 22.07 ± 0.20 | 0.402 | M |
| 23.17 ± 0.20 | 0.384 | M. |

3. The process of claim 2, wherein the light olefins are ethylene, propylene, butylene, or mixtures thereof.

4. The process of claim 2, wherein the oxygenate is methanol, dimethyl ether, or a mixture thereof.

5. A process for producing methylamine or dimethylamine comprising reacting methanol, dimethyl ether, or a mixture thereof, and ammonia in the gaseous phase in the presence of a catalyst comprising a molecular sieve having, in its calcined form, an X-ray diffraction pattern including the lines listed in the following table:

| 2-Theta | d-Spacing, nm | Relative Intensity |
| --- | --- | --- |
| 7.50 ± 0.20 | 1.177 | W |
| 8.65 ± 0.20 | 1.021 | W |
| 9.47 ± 0.20 | 0.933 | VS |
| 9.94 ± 0.20 | 0.889 | M |
| 13.47 ± 0.20 | 0.657 | M |
| 14.86 ± 0.20 | 0.596 | M |
| 16.07 ± 0.20 | 0.551 | W |
| 16.37 ± 0.20 | 0.541 | W |
| 17.92 ± 0.20 | 0.495 | W |
| 19.92 ± 0.20 | 0.445 | W |
| 20.66 ± 0.20 | 0.430 | W |
| 21.14 ± 0.20 | 0.420 | W |
| 21.34 ± 0.20 | 0.416 | W |
| 22.07 ± 0.20 | 0.402 | M |
| 23.17 ± 0.20 | 0.384 | M. |

6. A process for the reduction of oxides of nitrogen contained in a gas stream, wherein the process comprises contacting the gas stream with a molecular sieve having, in its calcined form, an X-ray diffraction pattern including the lines listed in the following table:

| 2-Theta | d-Spacing, nm | Relative Intensity |
| --- | --- | --- |
| 7.50 ± 0.20 | 1.177 | W |
| 8.65 ± 0.20 | 1.021 | W |
| 9.47 ± 0.20 | 0.933 | VS |
| 9.94 ± 0.20 | 0.889 | M |
| 13.47 ± 0.20 | 0.657 | M |
| 14.86 ± 0.20 | 0.596 | M |
| 16.07 ± 0.20 | 0.551 | W |
| 16.37 ± 0.20 | 0.541 | W |
| 17.92 ± 0.20 | 0.495 | W |
| 19.92 ± 0.20 | 0.445 | W |
| 20.66 ± 0.20 | 0.430 | W |
| 21.14 ± 0.20 | 0.420 | W |
| 21.34 ± 0.20 | 0.416 | W |
| 22.07 ± 0.20 | 0.402 | M |
| 23.17 ± 0.20 | 0.384 | M. |

7. The process of claim 6, conducted in the presence of oxygen.

8. The process of claim 6, wherein the molecular sieve contains one or more metals selected from the group consisting of Cr, Mn, Re, Mo, Fe, Ru, Co, Rh, Ir, Ni, Pd, Pt, Cu, Ag, Zn, Ga, In, Sn, and mixtures thereof.

9. The process of claim 8, wherein the metal is present in an amount of from 0.01 to 6 wt. %, based on the total weight of the molecular sieve.

10. A process for treating exhaust gas that comprises a hydrocarbon combustion product, the method comprising:
   (a) contacting the exhaust gas with a molecular sieve for a period of time effective to facilitate adsorption of the hydrocarbon combustion product by the molecular sieve;
   (b) passing a purge gas through the molecular sieve to remove adsorbed hydrocarbon combustion product therefrom; and
   (c) contacting the purge gas containing the removed hydrocarbon combustion product with a hydrocarbon conversion catalyst;
   wherein the molecular sieve has in its calcined form, an X-ray diffraction pattern including the lines listed in the following table:

| 2-Theta | d-Spacing, nm | Relative Intensity |
| --- | --- | --- |
| 7.50 ± 0.20 | 1.177 | W |
| 8.65 ± 0.20 | 1.021 | W |
| 9.47 ± 0.20 | 0.933 | VS |
| 9.94 ± 0.20 | 0.889 | M |
| 13.47 ± 0.20 | 0.657 | M |
| 14.86 ± 0.20 | 0.596 | M |
| 16.07 ± 0.20 | 0.551 | W |
| 16.37 ± 0.20 | 0.541 | W |
| 17.92 ± 0.20 | 0.495 | W |
| 19.92 ± 0.20 | 0.445 | W |
| 20.66 ± 0.20 | 0.430 | W |
| 21.14 ± 0.20 | 0.420 | W |
| 21.34 ± 0.20 | 0.416 | W |
| 22.07 ± 0.20 | 0.402 | M |
| 23.17 ± 0.20 | 0.384 | M. |

11. The process of claim 10, wherein the exhaust gas contains a plurality of hydrocarbon combustion products.

12. The process of claim 10, wherein the hydrocarbon combustion product is derived from the combustion of hydrocarbon fuel in an engine.

13. The process of claim 12, wherein the engine is an internal combustion engine.

14. The process of claim 13, wherein the internal combustion engine includes an exhaust system and the process is utilized to reduce cold start emission of hydrocarbons from the exhaust system.

15. The process of claim 10, wherein the molecular sieve contains a metal cation selected from the group consisting of Mg, Ca, Mn, Fe, Co, Ni, Pd, Pt, Cu, Ag, Au, Zn, Cd, and mixtures thereof.

* * * * *